(12) United States Patent
Knopp et al.

(10) Patent No.: US 7,548,311 B2
(45) Date of Patent: Jun. 16, 2009

(54) METHOD AND APPARATUS FOR CONDUCTING RAMAN SPECTROSCOPY

(75) Inventors: Kevin J. Knopp, Newburyport, MA (US); Peidong Wang, Carlisle, MA (US); Masud Azimi, Belmont, MA (US); Daryoosh Vakhshoori, Cambridge, MA (US)

(73) Assignee: Ahura Corporation, Wilmington, MA (US)

( * ) Notice: Subject to any disclaimer, the term of this patent is extended or adjusted under 35 U.S.C. 154(b) by 113 days.

(21) Appl. No.: 11/475,582

(22) Filed: Jun. 27, 2006

(65) Prior Publication Data

US 2007/0002319 A1  Jan. 4, 2007

Related U.S. Application Data

(63) Continuation-in-part of application No. 11/117,940, filed on Apr. 29, 2005.

(60) Provisional application No. 60/694,385, filed on Jun. 27, 2005.

(51) Int. Cl.
*G01J 3/44* (2006.01)
(52) U.S. Cl. .................................................. 356/301
(58) Field of Classification Search .................. 356/301
See application file for complete search history.

(56) References Cited

U.S. PATENT DOCUMENTS

| | | |
|---|---|---|
| 3,017,513 A | 1/1962 | Messelt |
| 3,906,241 A | 9/1975 | Thompson |
| 5,026,160 A | 6/1991 | Dorain et al. |
| 5,048,959 A | 9/1991 | Morris et al. |
| 5,377,004 A | 12/1994 | Owen et al. |
| 5,416,321 A * | 5/1995 | Sebastian et al. ............ 250/288 |
| 5,483,337 A | 1/1996 | Barnard et al. |
| 5,615,673 A | 4/1997 | Berger et al. |
| 5,651,018 A | 7/1997 | Mehuys et al. |
| 5,734,165 A | 3/1998 | Unal et al. |
| 5,828,450 A | 10/1998 | Dou et al. |
| 6,038,363 A | 3/2000 | Slater et al. |
| 6,045,502 A | 4/2000 | Eppstein et al. |
| 6,069,689 A | 5/2000 | Zeng et al. |

(Continued)

OTHER PUBLICATIONS

Eckenrode, Brian A. et al., Portable Raman Spectroscopy Systems for Field Analysis, Forensic Science Communications, Oct. 2001, vol. 3, No. 4.

(Continued)

*Primary Examiner*—Kara E Geisel
(74) *Attorney, Agent, or Firm*—Fish & Richardson P.C.

(57) ABSTRACT

A Raman probe assembly comprises: a light source for generating laser excitation light; a camera for capturing an image; a light analyzer for analyzing a Raman signature; and a light path for (i) delivering the laser excitation light from the light source to the specimen so as to produce the Raman signature for the specimen, (ii) capturing an image of the specimen and directing that image to the camera, and (iii) directing the Raman signature of the specimen to the light analyzer. A method includes providing a Raman probe assembly carried by a remote controlled robot; navigating the remote control robot to a position adjacent to a specimen; opening a shutter/wiper disposed adjacent to a window of the Raman analyzer; using a camera to aim the probe body at the specimen; energizing a light source; and analyzing the return light passed to the light analyzer.

18 Claims, 10 Drawing Sheets

U.S. PATENT DOCUMENTS

| | | | |
|---|---|---|---|
| 6,082,724 | A | 7/2000 | Kahlig et al. |
| 6,249,349 | B1 | 6/2001 | Lauer |
| 6,303,934 | B1 | 10/2001 | Daly et al. |
| 6,608,677 | B1 | 8/2003 | Ray et al. |
| 6,621,574 | B1 * | 9/2003 | Forney et al. ............... 356/301 |
| 6,636,304 | B2 | 10/2003 | Gilby |
| 6,707,548 | B2 | 3/2004 | Kreimer et al. |
| 6,803,328 | B2 | 10/2004 | McCullough |
| 6,862,092 | B1 | 3/2005 | Ibsen et al. |
| 6,907,149 | B2 | 6/2005 | Slater |
| 6,977,723 | B2 | 12/2005 | Lemmo et al. |
| 7,110,109 | B2 | 9/2006 | Knopp et al. |
| 7,148,963 | B2 | 12/2006 | Owen et al. |
| 2002/0033944 | A1 | 3/2002 | Sharts et al. |
| 2002/0101019 | A1 | 8/2002 | Boss |
| 2003/0002548 | A1 | 1/2003 | Boscha |
| 2003/0002839 | A1 | 1/2003 | Clow et al. |
| 2003/0085348 | A1 | 5/2003 | Megerie |
| 2003/0138940 | A1 * | 7/2003 | Lemmo et al. ........... 435/287.1 |
| 2003/0142302 | A1 * | 7/2003 | Jiang ......................... 356/301 |
| 2003/0147593 | A1 | 8/2003 | Slater |
| 2003/0197860 | A1 | 10/2003 | Rice |
| 2003/0227628 | A1 | 12/2003 | Kreimer et al. |
| 2004/0039274 | A1 | 2/2004 | Benaron et al. |
| 2004/0109230 | A1 | 6/2004 | Matsuhita et al. |
| 2004/0130714 | A1 | 7/2004 | Gellerman et al. |
| 2004/0165183 | A1 | 8/2004 | Marquardt et al. |
| 2004/0165254 | A1 | 8/2004 | Tokura et al. |
| 2004/0252299 | A9 | 12/2004 | Lemmo et al. |
| 2004/0254479 | A1 * | 12/2004 | Fralick et al. ............... 356/301 |
| 2004/0263843 | A1 | 12/2004 | Knopp et al. |
| 2005/0083521 | A1 | 4/2005 | Kamerman |
| 2006/0023209 | A1 | 2/2006 | Lee et al. |
| 2006/0170917 | A1 | 8/2006 | Vakhshoori et al. |
| 2007/0002319 | A1 | 1/2007 | Knopp et al. |
| 2007/0024848 | A1 | 2/2007 | Knopp et al. |

OTHER PUBLICATIONS

Harvey, S.D. et al., Blind field test evaluation of Raman spectroscopy as a forensic tool, Forensic Science International, 2002, 12-21, 125.

Moore, D.S., Instrumentation for trace detection of high explosives, Aug. 2004, 2499-2512, vol. 75, No. 8.

* cited by examiner

METHOD AND APPARATUS FOR CONDUCTING RAMAN SPECTROSCOPY

REFERENCE TO PENDING PRIOR PATENT APPLICATIONS

This patent application:

(i) is a continuation-in-part of pending prior U.S. patent application Ser. No. 11/117,940, filed Apr. 29, 2005 by Peidong Wang et al. for METHOD AND APPARATUS FOR CONDUCTING RAMAN SPECTROSCOPY; and (ii) claims benefit of pending prior U.S. Provisional Patent Application Ser. No. 60/694,385, filed Jun. 27, 2005 by Kevin J. Knopp et al. for RAMAN IDENTIFICATION SYSTEM.

The two above-identified patent applications are hereby incorporated herein by reference.

FIELD OF THE INVENTION

This invention relates to methods and apparatus for identifying and characterizing substances in general, and more particularly to methods and apparatus for identifying and characterizing substances using Raman spectroscopy.

BACKGROUND OF THE INVENTION

Raman spectroscopy is a viable technique for identifying and characterizing a vast array of substances. Raman spectroscopy is widely used in the scientific, commercial and public safety areas.

Recent technological advances are making it possible to increase the range of applications using Raman spectroscopy through a reduction in cost and size. For example, portable units have recently become available for field uses such as the on-site identification of potentially hazardous substances.

Unfortunately, with Raman spectroscopy, it is generally desirable to bring the optical probe to a position adjacent to the specimen when conducting the Raman spectroscopy. However, this can be a problem in view of the potentially hazardous materials which are to be analyzed, e.g., explosives, chemical agents, toxic industrial chemicals, etc.

Accordingly, a primary object of the present invention is to provide an improved Raman spectroscopy system which overcomes the aforementioned shortcomings of currently available systems.

SUMMARY OF THE INVENTION

In one preferred embodiment of the present invention, there is provided an improved Raman probe system in which a remote Raman probe assembly is mounted to a remote control robot for unmanned delivery to a remote specimen. The remote Raman probe assembly includes a wireless communication feature for transmitting information from the remote Raman probe assembly to a base unit. If desired, the wireless communication feature can take the form of a wireless Web link, so as to simplify communication transmission. Furthermore, the remote Raman probe assembly may comprise a Raman probe which may be attached to a robot arm, with the remainder of the remote Raman probe assembly being mounted to the body of the robot, such that the Raman probe can be selectively positioned vis-à-vis the specimen.

In another form of the present invention, there is provided a Raman probe assembly for analyzing a specimen, comprising:

a light source for generating laser excitation light;
a camera for capturing an image;
a light analyzer for analyzing a Raman signature; and
a light path for (i) delivering the laser excitation light from the light source to the specimen so as to produce the Raman signature for the specimen, (ii) capturing an image of the specimen and directing that image to the camera, and (iii) directing the Raman signature of the specimen to the light analyzer.

In another form of the present invention, there is provided a Raman probe assembly for analyzing a specimen, comprising:

a light source for generating laser excitation light;
a camera for capturing an image;
a light analyzer for analyzing a Raman signature;
a first light path for delivering the laser excitation light from the light source to the specimen so as to produce the Raman signature for the specimen;
a second light path for capturing an image of the specimen and directing that image to the camera;
a third light path for directing the Raman signature of the specimen to the light analyzer;
wherein the a least a portion of the first light path, the second light path and the third light path are coaxial with one another.

In another form of the present invention, there is provided a Raman probe assembly for analyzing a specimen, comprising:

a light source for generating laser excitation light;
a light analyzer for analyzing a Raman signature;
a light path for (i) delivering the laser excitation light from the light source to the specimen so as to produce the Raman signature for the specimen, and (ii) directing the Raman signature of the specimen to the light analyzer;
wherein the assembly further comprises a probe body for housing the at least a portion of the light path, and a window, with the light path extending through the window;
and further wherein the probe body further comprises a shutter/wiper disposed adjacent to the window.

In another form of the present invention, there is provided a Raman probe assembly for analyzing a specimen, comprising:

a light source for generating laser excitation light;
a light analyzer for analyzing a Raman signature;
a light path for (i) delivering the laser excitation light from the light source to the specimen so as to produce the Raman signature for the specimen, and (ii) directing the Raman signature of the specimen to the light analyzer; and
wherein the light analyzer comprises a transmitter for transmitting information using an Internet Web protocol.

In another form of the present invention, there is provided a method for identifying the nature of a specimen, the method comprising:

providing a Raman probe assembly comprising:
a light source for generating laser excitation light;
a camera for capturing an image;
a light analyzer for analyzing a Raman signature;
a light path for (i) delivering the laser excitation light from the light source to the specimen so as to produce the Raman signature for the specimen, (ii) capturing an image of the specimen and directing that image to the camera, and (iii) directing the Raman signature of the specimen to the light analyzer
wherein the assembly further comprises a probe body for housing the at least a portion of the light path, and a window, with the light path extending through the window;
wherein the probe body further comprises a shutter/wiper disposed adjacent to the window;

wherein the assembly is carried by a remote controlled robot;

providing a base station for receiving the image, and for remotely controlling the robot, and for receiving information from the light analyzer;

navigating the remote control robot from the base station to a position adjacent to the specimen;

opening the shutter/wiper;

using the camera to aim the probe body at the specimen;

energizing the light source so that the laser excitation light is directed at the specimen; and analyzing the return light passed to the light analyzer so as to determine of the nature of the specimen.

BRIEF DESCRIPTION OF THE DRAWINGS

These and other objects and features of the present invention will be more fully disclosed or rendered obvious by the following detailed description of the preferred embodiments of the invention, which is to be considered together with the accompanying drawings wherein like numbers refer to like parts and further wherein.

DETAILED DESCRIPTION OF THE PREFERRED EMBODIMENTS

Figure 1:
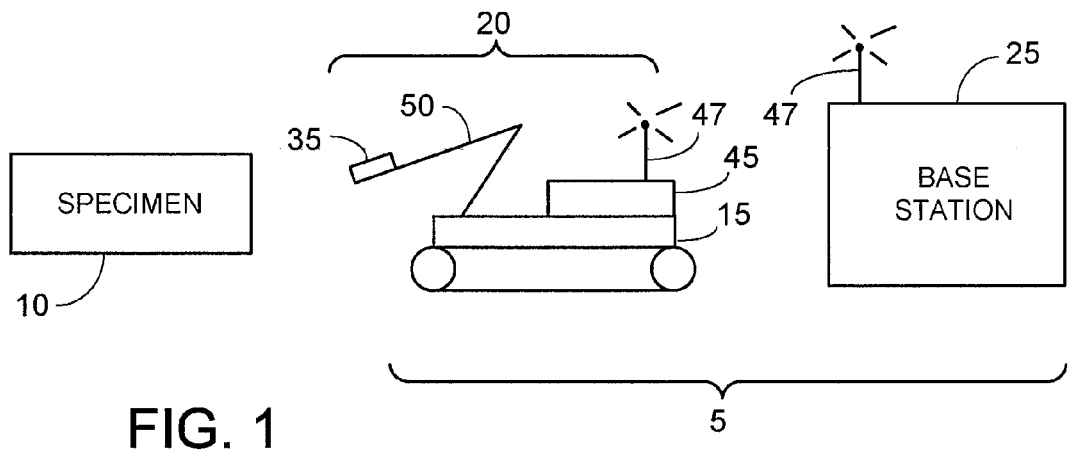
FIG. 1 is a schematic view of a novel Raman probe system formed in accordance with the present invention.

Looking first at FIG. 1, there is shown a novel Raman probe system 5 for conducting remote sensing of a specimen 10. Novel Raman probe system 5 generally comprises a remote control robot 15 for piloting a remote Raman probe assembly 20 to a position adjacent to specimen 10, and a base station 25 for controlling operation of remote control robot 15 and for receiving specimen analysis information from remote Raman probe assembly 20.

Remote control robot 15 may be any remote control robot of the sort well known in the art of remote transport, remote sensing, remote bomb disposal, etc. By way of example but not limitation, remote control robot 15 may be a tracked vehicle remotely controlled by base station 25, e.g., by radio control of the sort well known in the art.

Figure 2:
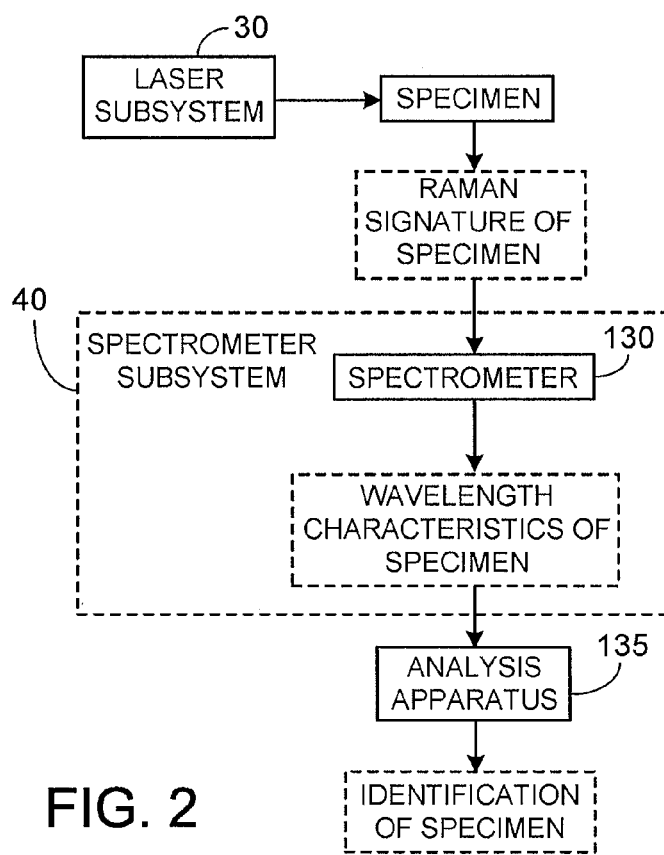
FIG. 2 is a schematic view of selected elements of the Raman probe system.
Figure 3:
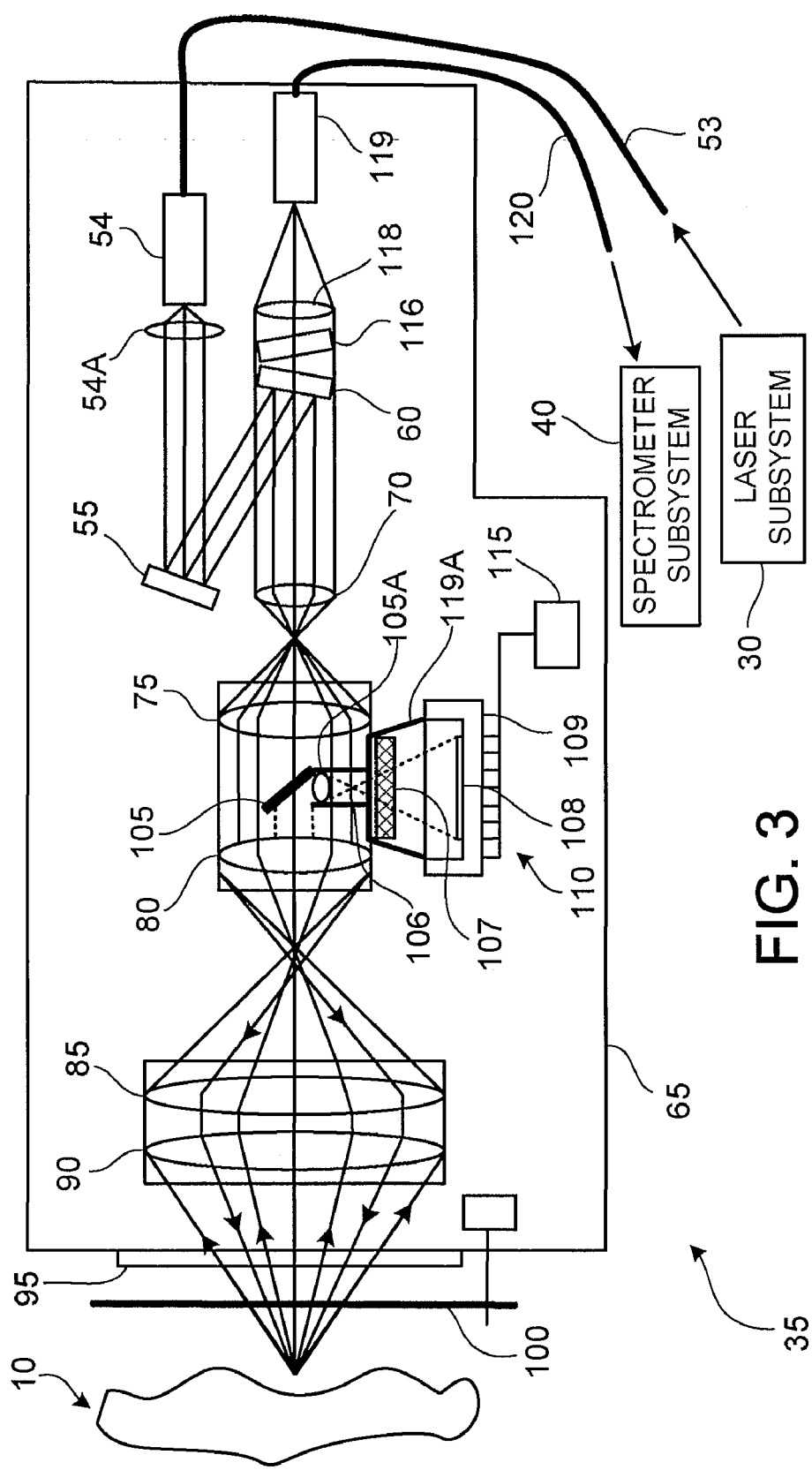
FIG. 3 is a schematic view of the Raman probe system's laser subsystem, optical probe subsystem and spectrometer subsystem.
Figure 4:
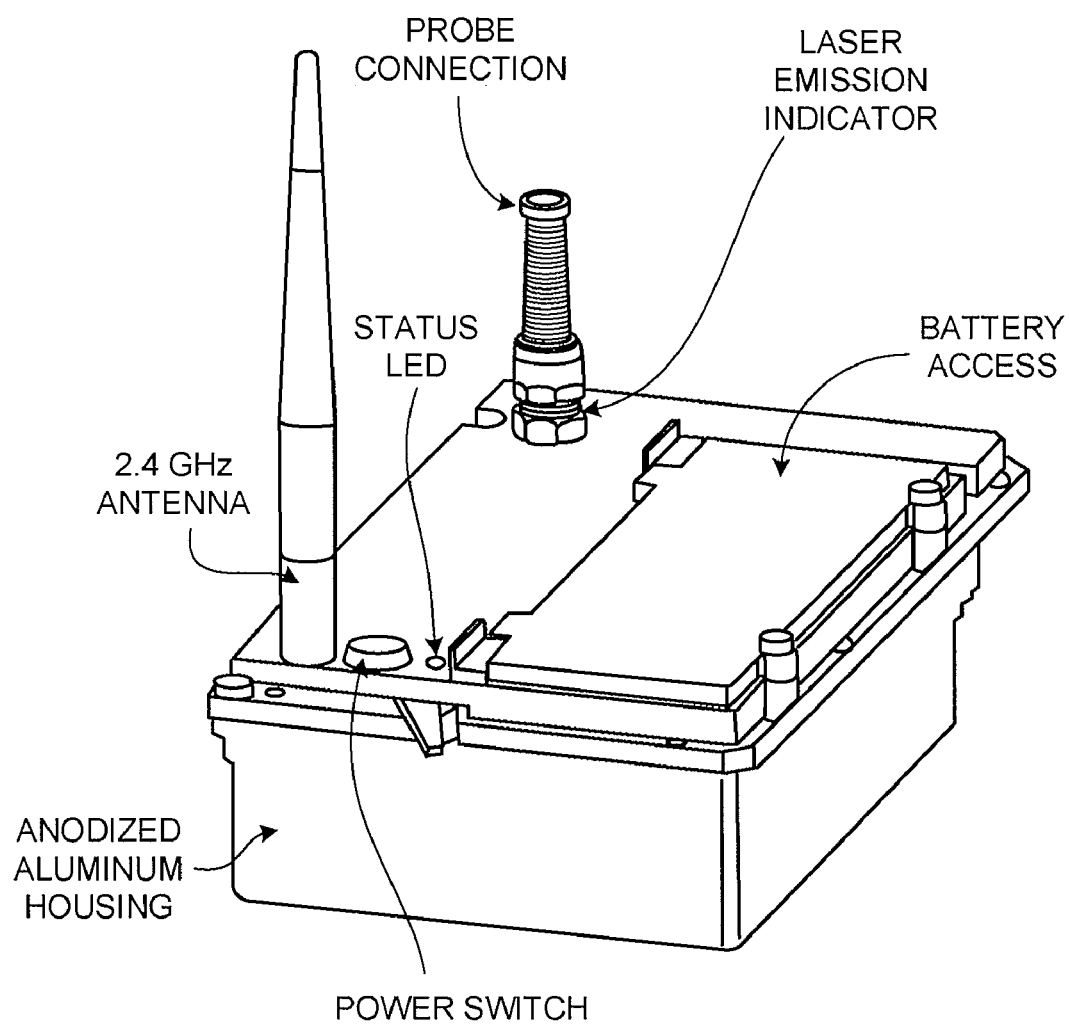
FIGS. 4-7 are schematic views of the optical control unit of the present invention.
Figure 7:
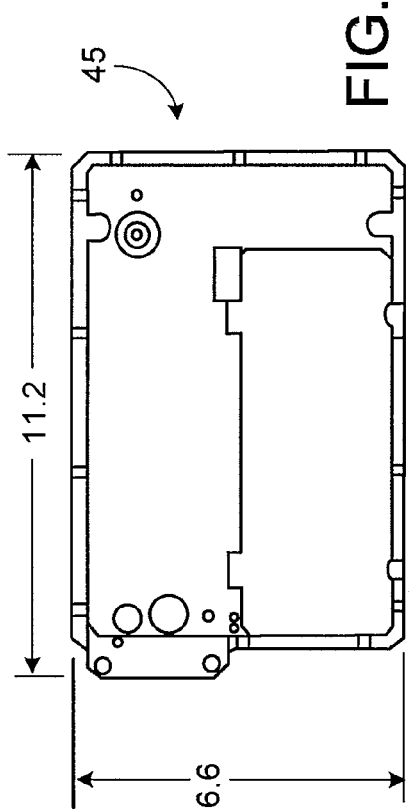
Figure 5:
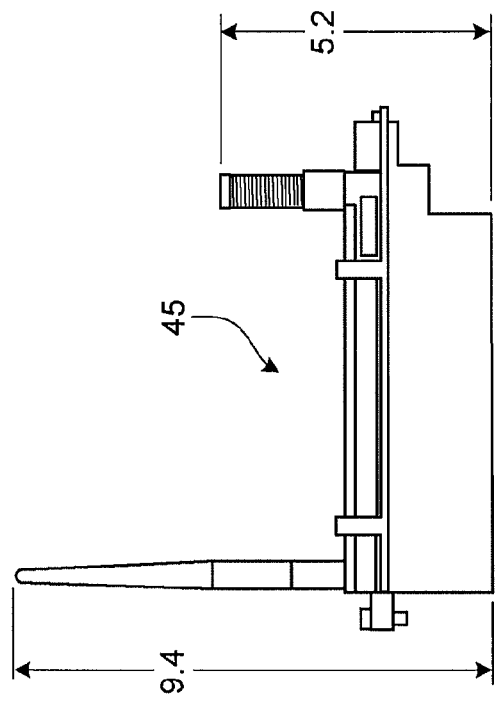
Figure 6:
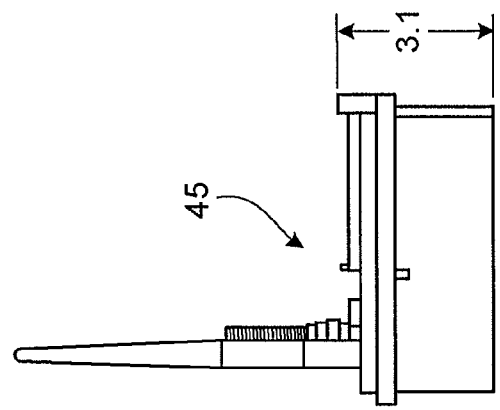
Figure 8:
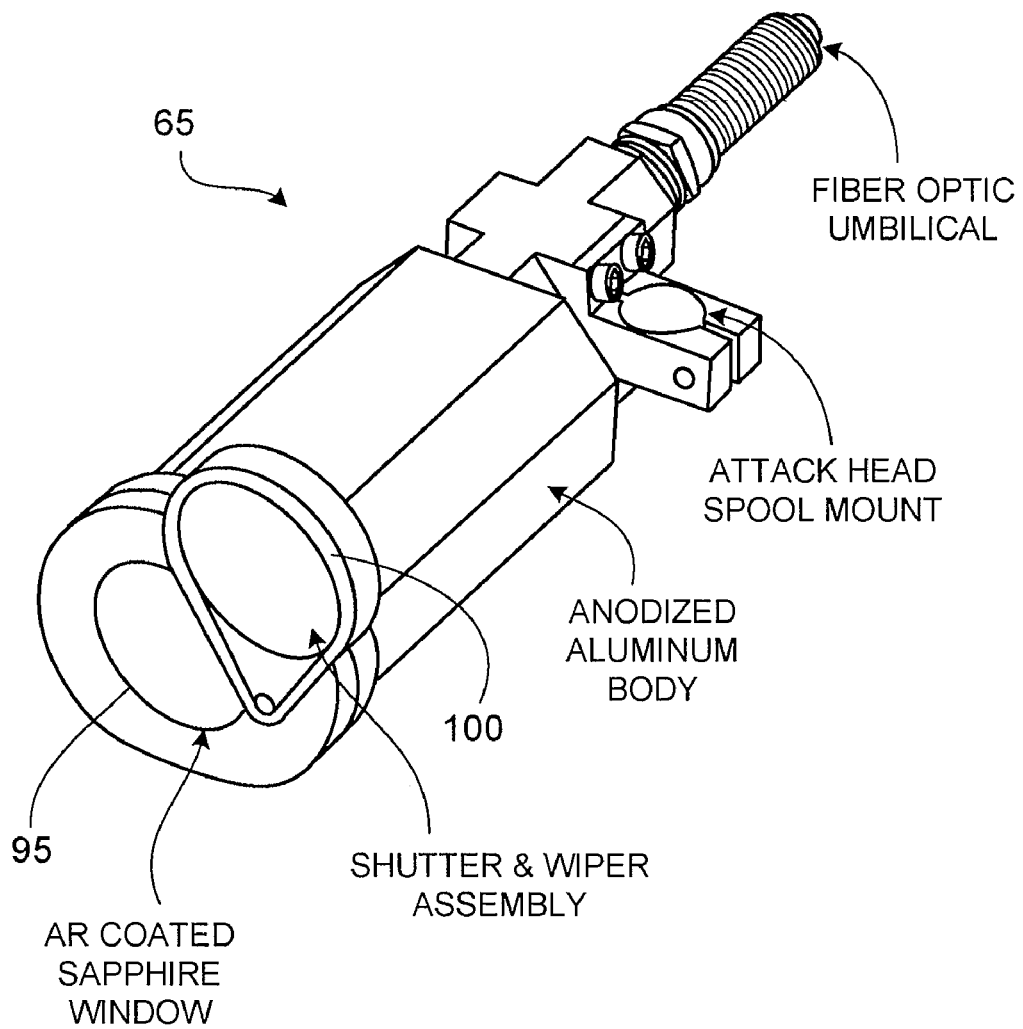
FIGS. 8-11 are schematic view of the Raman probe of the present invention.
Figure 11:
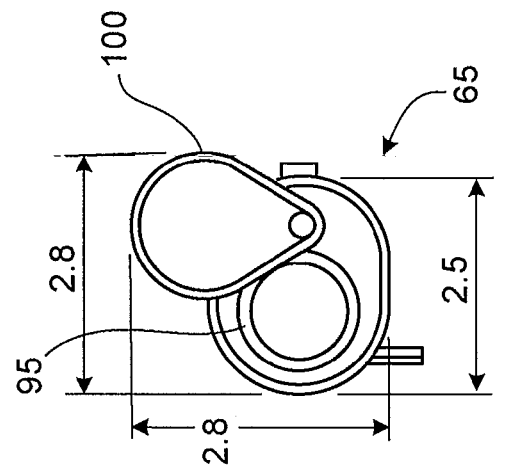
Figure 10:
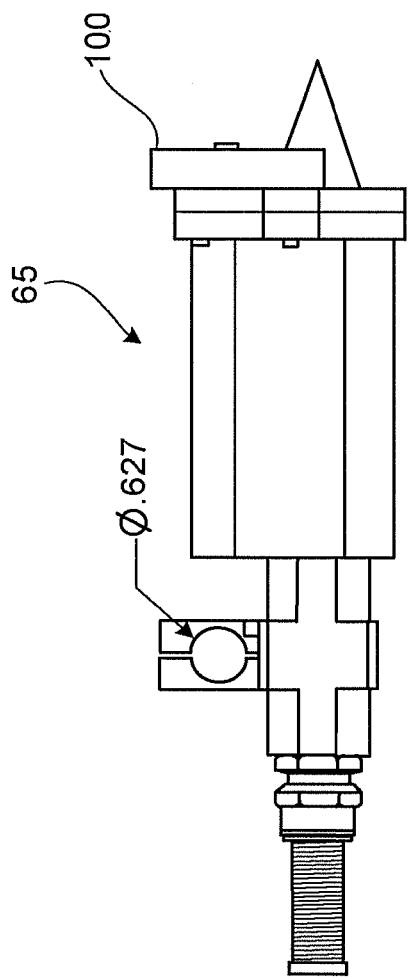
Figure 9:
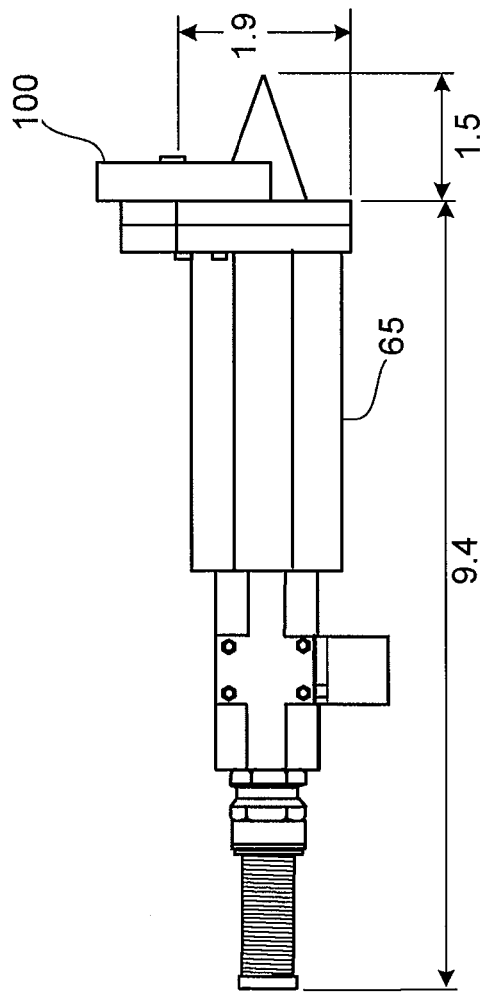

Looking now at FIGS. 1-3, remote Raman probe assembly 20 generally comprises a laser subsystem 30 (FIGS. 2 and 3) for generating the Raman pump signal, an optical probe subsystem 35 (FIG. 3) for delivering the Raman pump signal to the specimen and for gathering the Raman signature from the specimen, and a spectrometer subsystem 40 (FIGS. 2 and 3) for analyzing the Raman signature of the specimen so as to determine the nature of the specimen, and for transmitting analysis data to base station 25.

For convenience, laser subsystem 30 and spectrometer subsystem 40 may be packaged into an optical control unit 45 (see FIGS. 4-7) which is mounted onto remote control robot 15 so as to be carried thereby. Optical control unit 45 may also house an onboard power supply (e.g., a battery) for powering remote control robot 15 and its payload. Furthermore, optical control unit 45 is preferably provided with a communication subsystem 47 for permitting remote control robot 15, and its payload, to communicate with base station 25.

Optical probe subsystem 35 is also mounted to remote control robot 15. Preferably optical probe subsystem 35 is mounted to an articulating arm 50 (FIG. 1) on remote control robot 15. Articulating arm 50 may be remotely controlled by base station 25, such that the working end of optical probe subsystem 35 may be appropriately positioned adjacent to the specimen 10, as will hereinafter be discussed.

Laser subsystem 30 may comprise any laser suitable for use in Raman spectroscopy. By way of example but not limitation, laser subsystem 30 may comprise one or more >300 mW, 785 nm semiconductor lasers with limited linewidths (e.g., ~2 cm$^{-1}$). The output of laser subsystem 30 is delivered into the excitation fiber (see below) of optical probe subsystem 35 for delivery to the specimen.

Optical probe subsystem 35 is shown in FIGS. 3 and 8-11. Optical probe subsystem 35 comprises an excitation fiber 53 (e.g., 100 micrometer core diameter, Low OH) which delivers the excitation light through a flat polished excitation fiber ferrule 54 (e.g., a 100 micrometer Core multimode fiber) and then through a laser collimating lens 54A (e.g., PCX, f=3 mm, D=3 mm) to a reflector 55 (e.g., for a 785 nm laser) and then to a notch filter 60 (e.g., OD>6) which also aligns the excitation light with the longitudinal axis of the Raman probe 65. The excitation light is then focused using focusing lens 70 (e.g., PCX, f=6 mm, D=3 mm) and then passed through a first pair of telescopic lenses 75, 80 (e.g., Achromat, f=19 mm, D=12.7 mm), a second pair of telescopic lenses 85, 90 (e.g., Achromat, f=45 mm, D=25 mm), and a window 95 for permitting the excitation light to pass out of the distal end of Raman probe 65 and onto specimen 10.

A shutter/wiper assembly 100 is disposed adjacent to window 95. Shutter/wiper assembly 100 is adapted to (i) selectively close off window 95 so as to protect the window (e.g., during storage and selected transit); and/or (ii) wiper off window 95 so as to keep it free of debris (e.g., during scanning in a dusty and/or debris-laden environment). Furthermore, shutter/wiper assembly 90 can be used to wiper away any of specimen 10 which might unintentionally stick to window 95, so as to help ensure that the specimen is not inadvertently carried away from the remote site by Raman probe system 5 at the conclusion of the analysis.

The excitation light from optical probe subsystem 35 engages specimen 10 and interacts with specimen 10 so as to produce the Raman signature of the specimen.

The light returning from specimen 10 (including but not limited to the Raman signature of the specimen) passes back through window 95, through lenses 90, 85 and then through lens 80. A beam splitter 105 (e.g., gold coated glass, 1.5×3.8 mm, 1 mm thick) then directs some of the returning light through an imaging lens 105A, through a CCD imaging lens aperture 106 (e.g., D=0.9 mm), through an infra red blocking filter 107 (e.g., to block 785 nm laser light and pass visible spectrum, OD>3) to CCD chip 108 on CCD active die 109 of CCD camera 110 driven by CCD electronics 115; and the remainder of the returning light (including the Raman signature of the specimen) is directed through lens 75, through focusing lens 70, through notch filters 60, 116 (e.g., OD>6), through a collection collimator lens 118 (e.g., PCX, f=4 mm, D=6 mm), through a flat polished collection fiber ferrule 119 (e.g., a 200 micrometer Core multimode fiber) and into collection fiber 120 (e.g., 200 micrometer core diameter, Low OH) for delivery to spectrometer subsystem 40. A shield 119A may be provided around CCD camera 110 for stray and laser light blocking.

Preferably, CCD camera 110 and CCD electronics 115 are constructed so as to provide streaming digital video output to base station 25. Preferably, CCD electronics 115 are contained in Raman probe 65 or, alternatively, some or all of CCD electronics 115 may be contained within optical control unit 45. In any case, CCD electronics 115 are carried by remote control robot 15.

Figure 12:
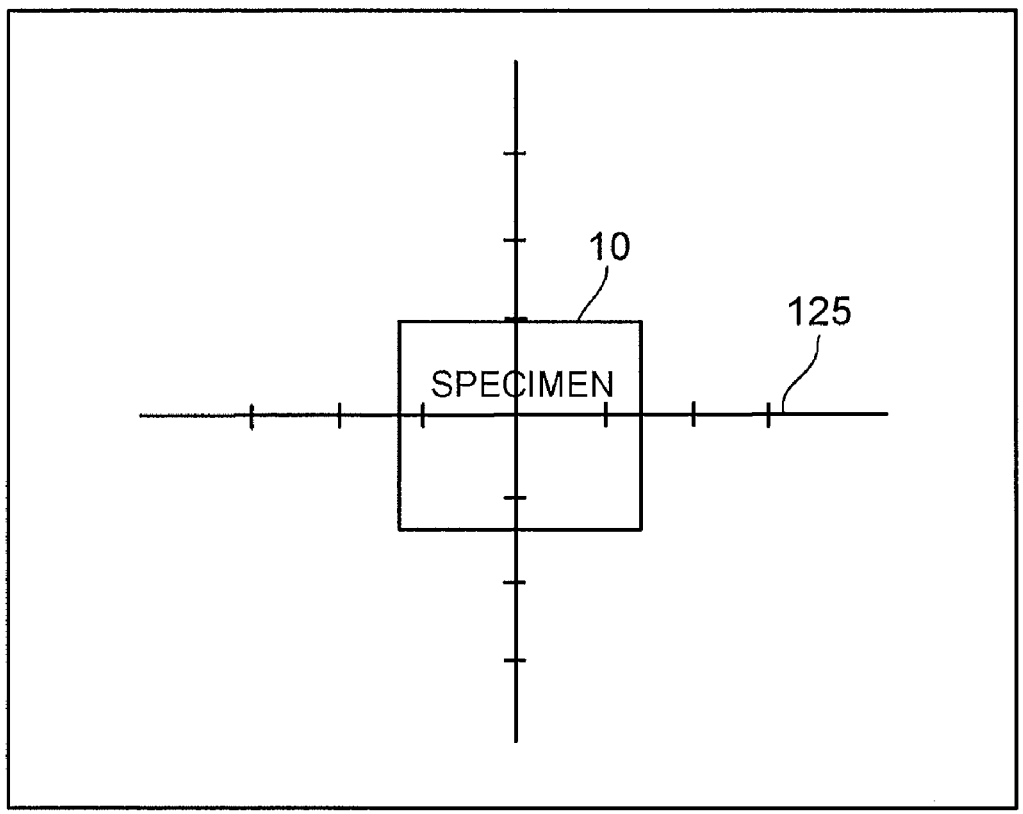
FIG. 12 is a schematic view showing the specimen being targeted through the probe.
Figure 13:
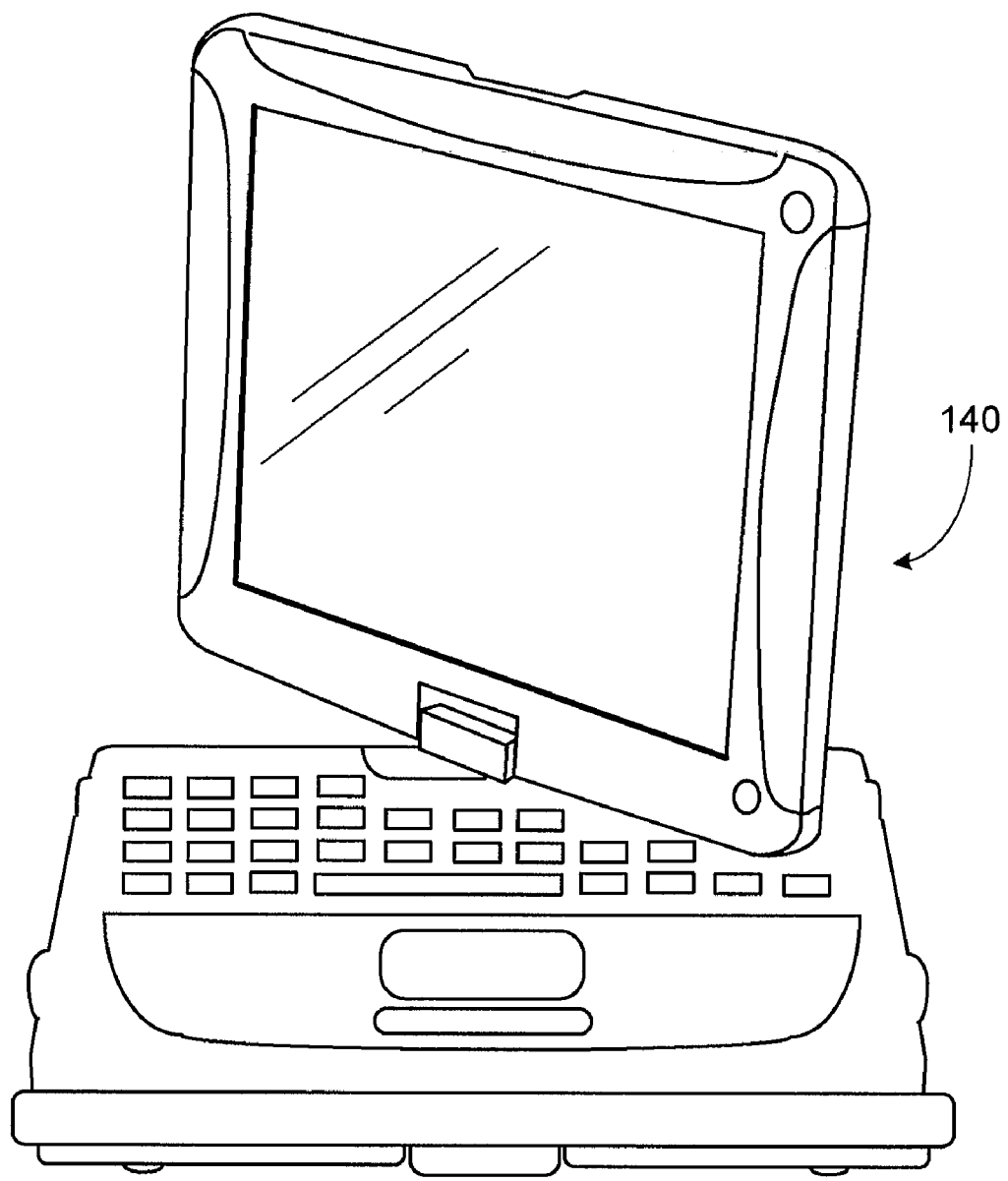
FIG. 13 is a schematic view of the system controller.

The output from CCD camera 110 is relayed to base station 25, whereby to permit a user at base station 25 to aim the Raman pump light on specimen 10. More particularly, and looking now at FIG. 12, CCD camera 110 and base station 25 can be configured to overlay cross-hairs 125 on the image provided by CCD camera 110, whereby to permit the user to maneuver articulating arm 50 so that the Raman pump light is directed onto specimen 10.

Spectrometer subsystem 40 generally comprises a spectrometer 130 for identifying the wavelength characteristics of the Raman signature of specimen 10. Spectrometer subsystem 40 sends the wavelength characteristics of the Raman signature of specimen 10 to analysis apparatus 135, which determines the nature of specimen 10 using the wavelength characteristics of the Raman signature. If desired, spectrometer 130 may comprise a dispersive spectrometer having a resolution of 7-10.5 cm$^{-1}$, a spectral range of 250-2800 cm$^{-1}$, and 2048 pixels.

Thus it will be appreciated that specimen analysis is conducted completely onboard remote control robot 15, and only the analysis results need be communicated to base station 25. However, in one preferred form of the invention, it is preferred that remote control robot 15 be configured to send base station 25 the Raman signature spectra, as well as the analysis results.

Base station 25 preferably comprises a system controller 140, preferably including a computer having appropriate user interface controls (e.g., a joystick, touch pad, etc.) for (i) controlling the operation of remote control robot 15, including its articulating arm 50; (ii) receiving the output from CCD camera 110, whereby to permit remote aiming of Raman probe 65; and (iii) receiving the analysis results from analysis apparatus 135.

If desired, Raman probe assembly 20 and base station 25 may also be provided with a Raman feedback loop, whereby to use the relative intensity of the Raman signature being obtained by the system so as to further improve alignment of Raman probe 65 with specimen 10. More particularly, base station 25 is configured so as to measure (either continuously or on a periodic basis) how much useful Raman signal is being collected by the system. Then, using a feedback loop, the intensity of the Raman signal can be used, in conjunction with cross-hairs 125, to help guarantee that Raman probe 65 is properly aimed at specimen 10.

In one preferred form of the invention, some or all of the communication links between (i) remote controlled robot 15 and/or its payload (i.e., Raman probe assembly 20, including CCD camera 110 and CCD electronics 115) and (ii) base station 25, may be effected via Internet Web-based protocols, e.g., the IEEE 802.11b wireless network standard.

If desired, remote control robot 15 can communicate analysis results, Raman spectra or any other information (e.g., CCD camera pictures) to a location other than, or in addition to, base station 25.

Use

Raman probe system 5 is preferably used as follows.

First, the user interface controls at base station 25 are used to navigate remote control robot 15, including its articulating arm 50, to position Raman probe 65 adjacent to specimen 10, e.g., within approximately 1 to 2 inches.

Then, shutter/wiper 100 is opened, and CCD camera 110 and CCD electronics 115 are used, in conjunction with the cross-hairs 125, to move articulating arm 50 so that Raman probe 65 is aimed at specimen 10 and positioned approximately 30 mm away from the specimen.

Then the Raman signature feedback system is used to optimize positioning of Raman probe 65 relative to specimen 10. This is done by energizing laser subsystem 30 so that Raman pump light is directed at specimen 10 and reading the intensity of the Raman signature returned from specimen 10, with a feedback loop driving the positioning of articulating arm 50, so as to optimize the position of Raman probe 65 relative to the specimen, whereby to provide the best possible Raman signature for the specimen.

Then, laser subsystem 30 is energized so that the Raman pump light is directed at specimen 10. The return light is passed to spectrometer 130, so as to determine the Raman signature of the specimen, and then the Raman signature is fed to analysis apparatus 135 for determination of the nature of the specimen. Analysis apparatus 135 then sends information regarding the nature of specimen 10 (optionally including the Raman spectra for specimen 10 as well) to base station 25.

Further Constructions

If desired, various modifications can be made to the foregoing construction without departing from the scope of the present invention.

Figure 14:
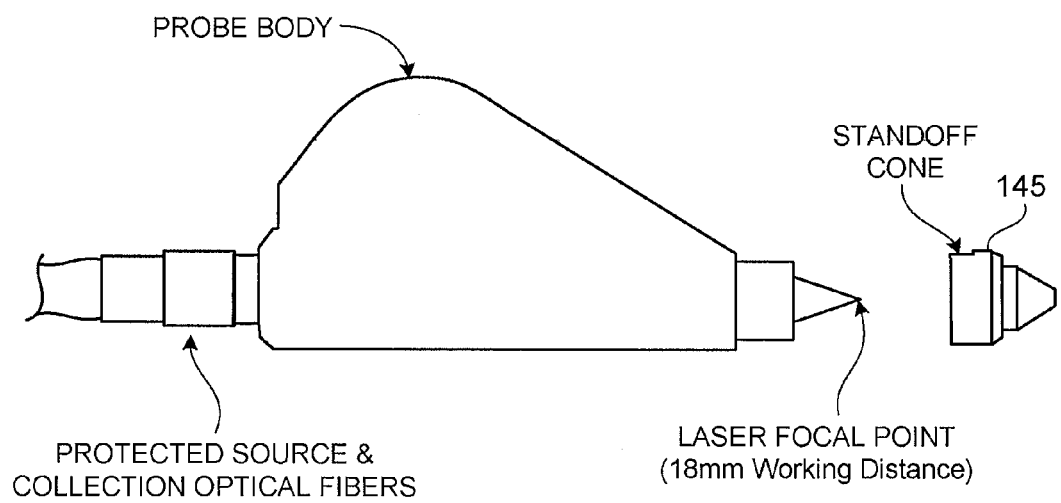
FIGS. 14 and 15 are schematic views showing a standoff cone used in conjunction with the optical probe assembly.
Figure 15:
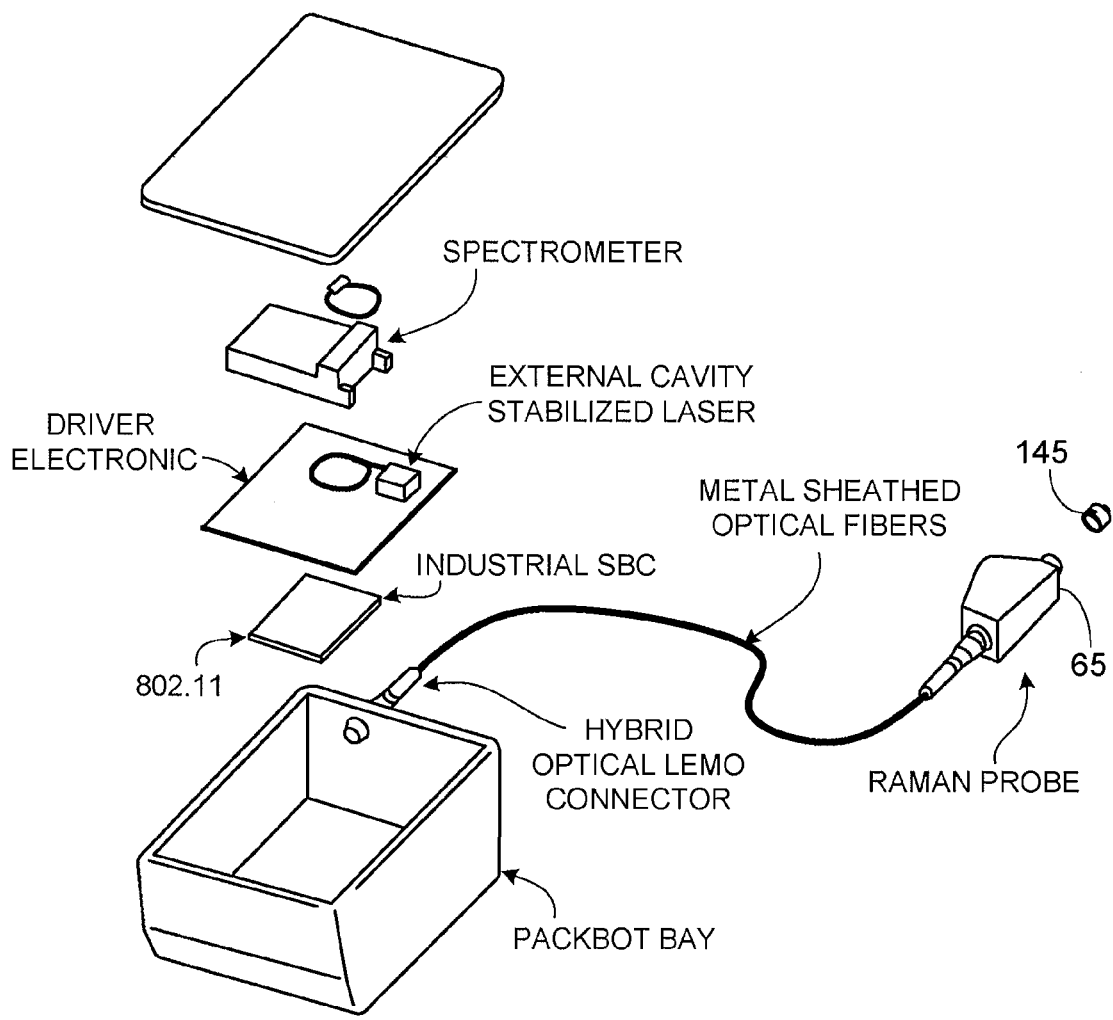

Thus, for example, and looking now at FIGS. 14 and 15, the shutter/wiper 100 may be replaced by a standoff cone 145. The standoff cone 145 can have various lengths, depending on whether specimen 10 is a solid or a liquid. More particularly, for solid specimens, standoff cone 145 is constructed so that when the distal tip of the standoff cone is positioned against the specimen, the focal point of the Raman laser will be located on the surface of the specimen. However, for liquid specimens, standoff cone 145 is constructed so that when the distal tip of the standoff cone is positioned against the specimen, the focal point of the Raman laser will be located on the within the body of the specimen.

It is to be understood that the present invention is by no means limited to the particular constructions herein disclosed and/or shown in the drawings, but also comprises any modifications or equivalents within the scope of the invention.

What is claimed is:

1. A Raman probe assembly for analyzing a specimen, comprising:
    a light source for generating laser excitation light;
    a camera for capturing an image;
    a light analyzer for analyzing a Raman signature;
    a light path for (i) delivering the laser excitation light from the light source to the specimen so as to produce the Raman signature for the specimen, (ii) capturing an image of the specimen and directing that image to the camera, and (iii) directing the Raman signature of the specimen to the light analyzer;
a remote control robot supporting the light source and the camera,
a base station operable to receive the image, to manually remotely control the robot, and to receive information from the light analyzer; and
a feedback mechanism operable to control the position of the remote control robot, and hence the assembly, relative to the specimen based on the intensity of the Raman signature.

2. A Raman probe assembly according to claim 1 wherein the camera comprises a video camera.

3. A Raman probe assembly according to claim 1 wherein the image comprises overlay cross-hairs.

4. A Raman probe assembly for analyzing a specimen, comprising:
a light source for generating laser excitation light;
a light analyzer for analyzing a Raman signature;
a light path for (i) delivering the laser excitation light from the light source to the specimen so as to produce the Raman signature for the specimen, and (ii) directing the Raman signature of the specimen to the light analyzer; and
a probe body housing at least a portion of the light path, the probe body comprising:
a window configured such that the light path extends through the window; and
a shutter/wiper disposed adjacent to the window, the shutter/wiper having a first position in which the shutter-wiper covers the window and a second position in which the window is exposed, the shutter/wiper operable to remove debris from a surface of the window.

5. A Raman probe assembly according to claim 4 wherein the light analyzer comprises a transmitter for transmitting information using an Internet Web protocol.

6. A Raman probe assembly according to claim 5 wherein the Internet Web protocol is the IEEE 802.11b wireless network standard.

7. A Raman probe assembly according to claim 4 wherein the light analyzer comprises a feedback mechanism utilizing the intensity of the Raman signature so as to permit optimized positioning of the assembly relative to the specimen.

8. A Raman probe assembly according to claim 7 wherein the assembly is mounted to remote control robot, and further wherein the feedback mechanism is used to control the position of the remote control robot, and hence the assembly, relative to the specimen.

9. A Raman probe assembly according to claim 4, further comprising:
a camera for capturing an image;
a light path for (i) delivering the laser excitation light from the light source to the specimen so as to produce the Raman signature for the specimen, (ii) capturing an image of the specimen and directing that image to the camera, and (iii) directing the Raman signature of the specimen to the light analyzer.

10. A Raman probe assembly according to claim 9 wherein the camera comprises a video camera.

11. A Raman probe assembly according to claim 9 wherein the image comprises overlay cross-hairs.

12. A Raman probe assembly according to claim 9 further comprising a remote controlled robot supporting the light source and the camera.

13. A Raman probe assembly according to claim 12 further comprising:
a base station operable to receive the image, to manually remotely control the robot, and to receive information from the light analyzer; and
a feedback mechanism operable to control the position of the remote control robot, and hence the assembly, relative to the specimen based on the intensity of the Raman signature.

14. A method for identifying the nature of a specimen, the method comprising:
providing a Raman probe assembly comprising:
a light source for generating laser excitation light;
a camera for capturing an image;
a light analyzer for analyzing a Raman signature;
a light path for (i) delivering the laser excitation light from the light source to the specimen so as to produce the Raman signature for the specimen, (ii) capturing an image of the specimen and directing that image to the camera, and (iii) directing the Raman signature of the specimen to the light analyzer
wherein the assembly further comprises a probe body for housing the at least a portion of the light path, and a window, with the light path extending through the window;
wherein the probe body further comprises a shutter/wiper disposed adjacent to the window;
wherein the assembly is carried by a remote controlled robot; providing a base station for receiving the image, and for remotely controlling the robot, and for receiving information from the light analyzer;
navigating the remote control robot from the base station to a position adjacent to the specimen;
opening the shutter/wiper;
using the camera to aim the probe body at the specimen;
energizing the light source so that the laser excitation light is directed at the specimen; and analyzing the return light passed to the light analyzer so as to determine the nature of the specimen.

15. A method according to claim 14 wherein the method further comprises:
after the energizing step and before the analyzing step, using the return light in a feed back step so as to further position the probe body relative to the specimen.

16. A method according to claim 15, wherein, during the feedback step, the base station continuously measures how much useful Raman signature is being obtained by the system.

17. A method according to claim 15, wherein, during the feedback step, the base station periodically measures how much useful Raman signature is being obtained by the system.

18. A method according to claim 14, further comprising removing debris from a surface of the window by movement of the shutter/wiper between a first position in which the shutter-wiper covers the window and a second position in which the window is exposed.

* * * * *

UNITED STATES PATENT AND TRADEMARK OFFICE
CERTIFICATE OF CORRECTION

PATENT NO. : 7,548,311 B2
APPLICATION NO. : 11/475582
DATED : June 16, 2009
INVENTOR(S) : Kevin J. Knopp et al.

Page 1 of 1

It is certified that error appears in the above-identified patent and that said Letters Patent is hereby corrected as shown below:

In Claim 4, at column 7, lines 30-31, delete "shutter-wiper" and insert
-- shutter/wiper --.

In Claim 18, at column 8, line 59, delete "shutter-wiper" and insert -- shutter/wiper --.

Signed and Sealed this

Eleventh Day of August, 2009

David J. Kappos
*Director of the United States Patent and Trademark Office*